(12) United States Patent
Teall

(10) Patent No.: US 6,448,229 B2
(45) Date of Patent: Sep. 10, 2002

(54) GAMMA SECRETASE INHIBITORS

(75) Inventor: Martin Richard Teall, Bishops Stortford (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/896,296

(22) Filed: Jun. 29, 2001

(30) Foreign Application Priority Data

Jul. 6, 2000 (GB) .............................. 0016681

(51) Int. Cl.⁷ .................... A61K 31/5375; A61P 25/28; C07D 265/28
(52) U.S. Cl. .......................... 514/19; 544/168
(58) Field of Search ............................ 544/168; 514/19

(56) References Cited

FOREIGN PATENT DOCUMENTS

WO          WO 9822494          5/1998

Primary Examiner—Robert W. Ramsuer
(74) Attorney, Agent, or Firm—J. Eric Thies; Shu Muk Lee; Melvin Winokur

(57) ABSTRACT

The invention provides compounds of formula (I) and pharmaceutically acceptable salts thereof:

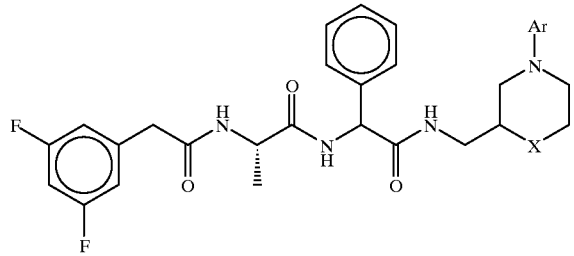

(I)

wherein X is $CH_2$, O or S. The compounds inhibit gamma secretase without affecting Notch signalling, and hence find use in the treatment or prevention of Alzheimer's disease.

9 Claims, No Drawings

GAMMA SECRETASE INHIBITORS

The present invention relates to compounds, their salts, pharmaceutical compositions comprising them, processes for making them and their use in treating Alzheimer's Disease.

Alzheimer's Disease (AD) is characterized by the abnormal deposition of amyloid in the brain in the form of extra-cellular plaques and intra-cellular neurofibrillary tangles. The rate of amyloid accumulation is a combination of the rates of formation, aggregation and egress from the brain. It is generally accepted that the main constituent of amyloid plaques is the 4 kD amyloid protein (βA4, also referred to as Aβ,β-protein and βAP) which is a proteolytic product of a precursor protein of much larger size. The ragged $NH_2$- and COOH-termini of the native Aβ amyloid indicates that a complex mechanism of proteolysis is involved in its biogenesis.

The amyloid precursor protein (APP or AβPP) has a receptor-like structure with a large ectodomain, a membrane spanning region and a short cytoplasmic tail. Different isoforms of APP result from the alternative splicing of three exons in a single gene and have 695,751 and 770 amino acids respectively.

The Aβ domain encompasses parts of both extra-cellular and transmembrane domains of APP, thus its release implies the existence of two distinct proteolytic events to generate its $NH_2$- and COOH-termini. At least two secretory mechanisms exist which release APP from the membrane and generate the soluble, COOH-truncated forms of APP ($APP_s$). Proteases which release APP and its fragments from the membrane are termed "secretases". Most $APP_s$ is released by a putative α-secretase which cleaves within the Aβdomain (between residues $Lys^{16}$ and $Leu^{17}$) to release (α-$APP_s$ and precludes the release of intact Aβ. A minor portion of $APP_s$ is released by a β-secretase, which cleaves near the $NH_2$-terminus of Aβ and produces COOH-terminal fragments (CTFs) which contain the whole Aβ domain. Finding these fragments in the extracellular compartment suggests that another proteolytic activity (γ-secretase) exists under normal conditions which can generate the COOH-terminus of Aβ.

It is believed that γ-secretase itself depends for its activity on the presence of presenilin-1. In a manner that is not fully understood presenilin-1 appears to undergo auto-cleavage.

The potential of γ-secretase inhibitors to inhibit the functioning of presinilins, which have been proposed as candidates γ-secretases, has raised questions over their suitability. In particular, signalling through the Notch pathway, important during embryonic development and in haematopoeisis, requires the presenilin-dependent proteolytic release of the Notch intracellular domain (NICD). Using a novel Xenopus developmental assay for Notch activity it has surprisingly been found that the present γ-secretase inhibitors do not prevent Notch signalling in-vivo.

The present compounds are structurally related to those disclosed in WO-A-9822494. However there is no discussion in that document of the problem of interference of Notch signalling nor any suggestion of how the provision of γ-secretase inhibitors that do not inhibit Notch signalling may be achieved.

Accordingly, the present invention provides a compound of formula I or a pharmaceutically acceptable salt thereof:

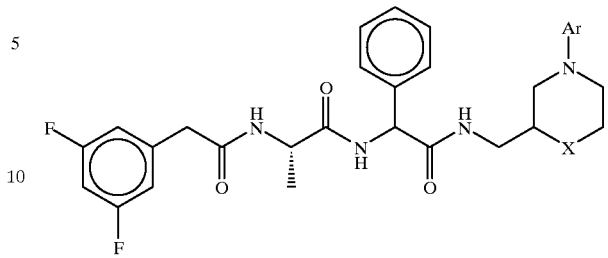

(I)

wherein: X is $CH_2$, oxygen or sulphur; and

Ar is phenyl optionally substituted by one, two or three substituents chosen from halogen, $C_{1-6}$alkyl, $C_{2-6}$alkenyl, $C_{2-6}$alkynyl, hydroxy, cyano, nitro, $NR^1R^2$ where $R^1$ and $R^2$ are independently hydrogen or $C_{1-6}$alkyl, $C_{1-6}$alkoxy, $C_{2-6}$alkenyloxy, $C_{2-6}$alkynyloxy, thiol, $C_{1-6}$alkylthio, $C_{2-6}$alkenylthio, $C_{2-6}$alkynylthio, $C_{1-6}$alkylcarbonyl, $C_{1-6}$alkoxycarbonyl, $C_{1-6}$haloalkyl, $C_{2-6}$haloalkenyl and $C_{2-6}$haloalkynyl.

Preferably X is oxygen.

Preferably Ar is optionally substituted by one, two or three substituents chosen from halogen, $C_{1-6}$alkyl, hydroxy, amino, $C_{1-6}$alkoxy, thiol, $C_{1-6}$alkoxycarbonyl and $C_{1-6}$haloalkyl.

More preferably Ar is optionally substituted by one substituent chosen from halogen, $C_{1-4}$alkyl, hydroxy, amino, $C_{1-4}$alkoxy, thiol, $C_{1-4}$alkoxycarbonyl and $C_{1-4}$haloalkyl.

In one embodiment Ar is unsubstituted.

A specific Example of the present invention is: 2-[2-(3,5-difluorophenyl)acetylamino]-N-{phenyl[(4-phenylmorpholin-2-ylmethyl)carbamoyl]methyl}propionamide and the pharmaceutically acceptable salts thereof.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl, isopropyl and t-butyl. Derived expressions such as "$C_{1-4}$alkyl", "$C_{2-6}$alkenyl" and "$C_{2-6}$alkynyl" are to be construed in an analogous manner.

The term "halogen" as used herein includes fluorine, chlorine, bromine and iodine, of which fluorine and chlorine are preferred.

As used herein the term "$C_{1-6}$alkoxy" includes methoxy and ethoxy groups, and straight-chained, branched and cyclic propoxy and butoxy groups, including cyclopropyl-methoxy. "$C_{2-6}$alkynyloxy", "$C_{2-6}$alkenyloxy", "$C_{1-6}$alkylthio", "$C_{2-6}$alkenylthio", "$C_{2-6}$alkynylthio" and "$C_{1-4}$alkoxy" are to be construed in analogous manner.

As used herein the term "$C_{1-6}$alkoxycarbonyl" includes methoxycarbonyl and alkoxycarbonyl groups and straight-chained, branched and cyclic propoxycarbonyl and butoxycarbonyl groups, including cyclopropylmethoxycarbonyl. "$C_{1-4}$alkoxycarbonyl" is to be construed in analogous manner.

Examples of pharmaceutically acceptable salts are hydrochlorides, sulfates, citrates, tartrates, acetates, methanesulfonates, phosphates, oxalates and benzoates.

The compounds of the present invention have an activity as inhibitors of γ secretase. In a preferred embodiment the compounds of the invention inhibit proteolysis of PS-1.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums or surfactants such as sorbitan monooleate, polyethylene glycel, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease. Preferably this treatment occurs without inhibiting Notch signalling.

The present invention further provides the use of a compound of the present invention or a pharmaceutically acceptable salt thereof in the manufacture of a medicament for treating or preventing Alzheimer's disease, preferably without inhibiting Notch signalling.

Also disclosed is a method of treatment of a subject suffering from or prone to Alzheimer's disease which comprises administering to that subject an effective amount of a compound according to the present invention or a pharmaceutically acceptable salt thereof. This method of treatment preferably does not inhibit Notch signalling.

The liquid forms in which the novel compositions of the present invention may be incorporated for administration orally or by injection include aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

For treating or preventing Alzheimer's Disease, a suitable dosage level is about 0.01 to 250 mg/kg per day, preferably about 0.01 to 100 mg/kg per day, and especially about 0.01 to 5 mg/kg of body weight per day. The compounds may be administered on a regimen of 1 to 4 times per day. In some cases, however, dosage outside these limits may be used.

There is also provided a process for producing a compound of formula I or a pharmaceutically acceptable salt thereof which comprises reacting a compound of formula II with a compound of formula III:

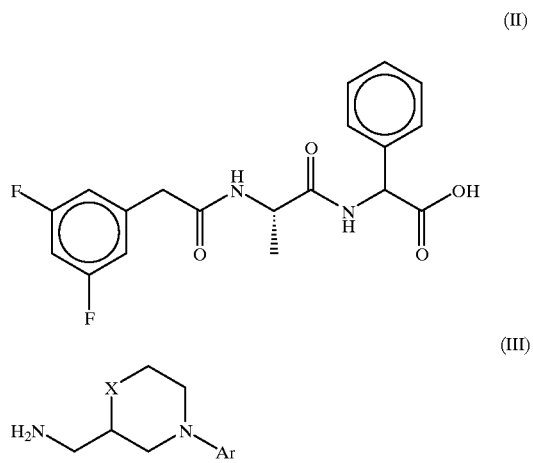

wherein X and Ar are as defined above, generally in the presence of a coupling agent such as 1-(3-dimethylaminopropyl)-3-ethylcarbodiimide, and hydroxybenzotriazole, generally in the presence of a base such as triethylamine, and a solvent such as tetrahydrofuran, for about 18 h at room temperature.

Compounds of formulae II and III are commercially available or can be made by known methods from commercially available compounds.

It will be understood that any compound of formula I initially obtained from the above process may, where appropriate, subsequently be elaborated into a further compound of formula I by techniques known from the art.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

A typical assay which can be used to determine the level of activity of compounds of the present invention is as follows:

(1) Mouse neuroblastoma neuro 2a cells expressing human app695 are cultured at 50–70% confluency in the presence of sterile 10 mM sodium butyrate.

(2) Cells are placed in 96-well plates at 30,000/well/100 μL in minimal essential medium (MEM) (phenol red-free)+ 10% foetal bovine serum (FBS), 50mM HEPES buffer (pH7.3), 1% glutamine, 0.2 mg/mL G418 antibiotic, 10 mM sodium butyrate.

(3) Make dilutions of the compound plate. Dilute stock solution to 5.5% DMSO/110 μM compound. Mix compounds vigorously and store at 4° C. until use.

(4) Add 10 μL compound/well. Mix plate briefly, and leave for 18 h in 37° C. incubator.

(5) Remove 90 μL of culture supernatant and dilute 1:1 with ice-cold 25mM HEPES (pH.3), 0.1% BSA, 1.0 mM EDTA (+broad spectrum protease inhibitor cocktail; pre-aliquotted into a 96-well plate). Mix and keep on ice or freeze at -80° C.

(6) Add back 100 μL of warm MEM +10% FBS, 50 mM HEPES (pH7.3), 1% glutamine, 0.2 mg/mL G418, 10 mM sodium butyrate to each well, and return plate to 37° C. incubator.

(7) Prepare reagents necessary to determine amyloid peptide levels, for example by ELISA assay (8) To determine if compounds are cytotoxic cell viability following compound administration is assessed by the use of redox dye reduction. A typical example is a combination of redox dye MTS (Promega) and the electron coupling reagent PES. This mixture is made up according to the manufacturer's instructions and left at room temperature.

(9) Quantitate amyloid beta 40 and 42 peptides using an appropriate volume of diluted culture medium by standard ELISA techniques.

(10) Add 15 μL/well MTS/PES solution to the cells; mix and leave at 37° C.

(11) Read plate when the absorbance values are approximately 1.0 (mix briefly before reading to disperse the reduced formazan product).

The Example of the present invention had an $ED_{50}$ of less than 500 nM in the above assay.

The following assay was used to determine the effect of compounds on Notch signalling.

Xenopus embryos were cultured in 1/10 NAM [Beck & Slack, Development, 126, 1611–1620, 1999] supplemented with protease inhibitors (200× stock in DMSO) from stage 15 [P. D. Nieuwkoop and J. Faber, Normal table of Xenopus laevis, Daudin 1967, Reprinted Garland 1994] (24 hours), to stage 40 (3 days). Control siblings were incubated in 1/10 NAM containing 0.05% DMSO. At 3 days they were fixed in batches of 20 and measured using a graduated eyepiece on a Wild dissecting microscope set to 25×. Each tadpole was measured from head to proctodaeum (head and trunk) and from proctodaeum to tail tip (tail). Tail buds were extirpated at stage 30 and cultured for 24 hours as described previously [Tucker & Slack, Development, 121, 249–262, 1995]. Somites were detected by staining with monoclonal antibody 12/101 [Kintner & Brockes, Nature, 308, 67–69, 1984], as described elsewhere [Tucker & Slack, 1995]. In situ hybridisation for Xhox3 has been previously described [Beck & Slack, Mech. Dev., 72, 41–52, 1998].

The Example of the present invention did not significantly inhibit tail bud formation.

The following Examples illustrate the present invention.

EXAMPLE 1

2-[2-(3,5-Difluorophenyl)acetylamino]-N-{phenyl[(4-phenylmorpholin-2-ylmethyl)carbamoyl]methyl}propionamide A mixture of [(3,5-Difluorophenyl)acetylamino]-1-ethylcarbamoyl-1-phenyl ethanoic acid (20 mg, 0.053 mmol), 1-(3-dimethylaminopropyl)-3-ethyl carbodiimide (11.2 mg, 0.058 mmol) and hydroxybenzotriazole (7.8 mg, 0.058 mmol) in tetrahydrofuran was treated with N-phenyl 2-aminomethyl morpholine (15.2 mg, 0.079 mmol) and triethylamine (16 mg, 0.159 mmol) and the reaction stirred for 18 hours at room temperature. Evaporation of the solvent and purification on a bond elute cartridge gave the product (6 mg). Mixture of diastereoisomers: ($^1$H, DMSO) 8.45–8.34 (3 H, m), 7.43–6.76 (10 H, m), 5.44 (1 H, t), 4.44 (1 H, t), 3.91 (1 H, br), 3.59–3.16 (11 H, m), 2.61 (1 H, dd), 2.26 (1 H,m), 1.22 (3 H, m) MS (CI+) MH+551.

What is claimed is:

1. A compound of formula I or a pharmaceutically acceptable salt thereof:

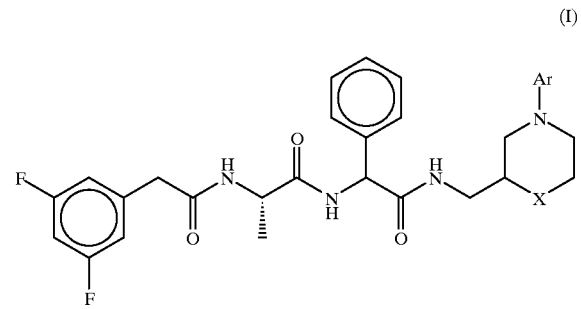

(I)

wherein: X is $CH_2$, oxygen or sulphur; and

Ar is phenyl optionally substituted by one, two or three substituents chosen from halogen, $C_{1-6}$alkyl, $C_{2-6}$alkenyl, $C_{2-6}$alkynyl, hydroxy, cyano, nitro, $NR^1R^2$ where $R^1$ and $R^2$ are independently hydrogen or $C_{1-6}$alkyl, $C_{1-6}$alkoxy, $C_{2-6}$alkenyloxy, $C_{2-6}$alkynyloxy, thiol, $C_{1-6}$alkylthio, $C_{2-6}$alkenylthio, $C_{2-6}$alkynylthio, $C_{1-6}$alkylcarbonyl, $C_{1-6}$alkoxycarbonyl, $C_{1-6}$haloalkyl, $C_{2-6}$haloalkenyl and $C_{2-6}$haloalkynyl.

2. A compound according to claim 1 wherein X is oxygen.

3. A compound according to claim 1 wherein Ar is optionally substituted by one, two or three substituents chosen from halogen, $C_{1-6}$alkyl, hydroxy, amino, $C_{1-6}$alkoxy, thiol, $C_{1-6}$alkoxycarbonyl and $C_{1-6}$haloalkyl.

4. A compound according to claim 3 wherein Ar is optionally substituted by one substituent chosen from halogen, $C_{1-4}$alkyl, hydroxy, amino, $C_{1-4}$alkoxy, thiol, $C_{1-4}$alkoxycarbonyl and $C_{1-4}$haloalkyl.

5. A compound according to claim 1 wherein Ar is unsubstituted.

6. A compound according to claim 1 selected from 2-[2-(3,5-difluorophenyl)acetylamino]-N-{phenyl[(4-phenylmorpholin-2-ylmethyl)carbamoyl]methyl}propionamide and the pharmaceutically acceptable salts thereof.

7. A pharmaceutical composition comprising one or more compounds according to claim 1 and a pharmaceutically acceptable carrier.

8. A method of treatment of a subject suffering from or prone to Alzheimer's disease which comprises administering to that subject an effective amount of a compound according to claim 1.

9. A method of treatment according to claim 8 which does not inhibit Notch signalling.

* * * * *